US009321783B2

(12) United States Patent
Ibert et al.

(10) Patent No.: US 9,321,783 B2
(45) Date of Patent: Apr. 26, 2016

(54) METHOD FOR PREPARING DIALKYLOXYDIANHYROHEXITOL BY ETHERIFICATION OF DIANHYDROHEXITOL USING A LIGHT ALCOHOL, IN THE PRESENCE OF AN ACIDIC CATALYST

(71) Applicants: ROQUETTE FRERES, Lestrem (FR); CENTRE NATIONAL DE LA RECHERCHE SCIENTIFIQUE - CNRS, Paris (FR); UNIVERSITE CLAUDE BERNARD LYON 1, Villeurbanne (FR)

(72) Inventors: Mathias Ibert, La Chapelle d'Armentieres (FR); Nadine Essayem, Saint Just Chaleyssin (FR); Cyril Feche, Leyment (FR); Alain Perrard, Saint-Foy-les-Lyon (FR)

(73) Assignees: ROQUETTE FRERES, Lestrem (FR); CENTRE NATIONAL DE LA RECHERCHE SCIENTIFIQUE-CNRS, Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 14/419,661

(22) PCT Filed: Aug. 5, 2013

(86) PCT No.: PCT/FR2013/051881
§ 371 (c)(1),
(2) Date: Feb. 5, 2015

(87) PCT Pub. No.: WO2014/023902
PCT Pub. Date: Feb. 13, 2014

(65) Prior Publication Data
US 2015/0203507 A1 Jul. 23, 2015

(30) Foreign Application Priority Data

Aug. 6, 2012 (FR) .................. 12 57621

(51) Int. Cl.
C07D 493/00 (2006.01)
C07D 493/04 (2006.01)

(52) U.S. Cl.
CPC .................. *C07D 493/04* (2013.01)

(58) Field of Classification Search
CPC .................................................. C07D 493/04
USPC .................................................. 549/464
See application file for complete search history.

(56) References Cited

U.S. PATENT DOCUMENTS 4,770,871 A 9/1988 Greenshields

FOREIGN PATENT DOCUMENTS

WO 2009120703 A2 10/2009

OTHER PUBLICATIONS

International Search Report, dated Oct. 2, 2013, from corresponding PCT application.

*Primary Examiner* — T. Victor Oh
(74) *Attorney, Agent, or Firm* — Young & Thompson

(57) ABSTRACT

A method for preparing a dialkyloxydianhyrohexitol (dimethylisosorbide) composition by etherification of dianhydrohexitol (isosorbide). The aim is to achieve a "clean" method that avoids the use of a methylation agent such as dimethyl sulfate or methyl chloride, which generates stoechiometric quantities of salts, or expensive dialkyl-carbonates, wherein only one of the two methyl groups participates in the preparation of mixed isosorbide ethers. The method involves using at least one O-alkylation agent and a catalyst including an acid or an acid salt, preferably a catalyst having Lewis or BrØnsted acid properties. A device for carrying out the method wherein the device includes a vaporization oven and a reaction oven is also described.

14 Claims, 1 Drawing Sheet

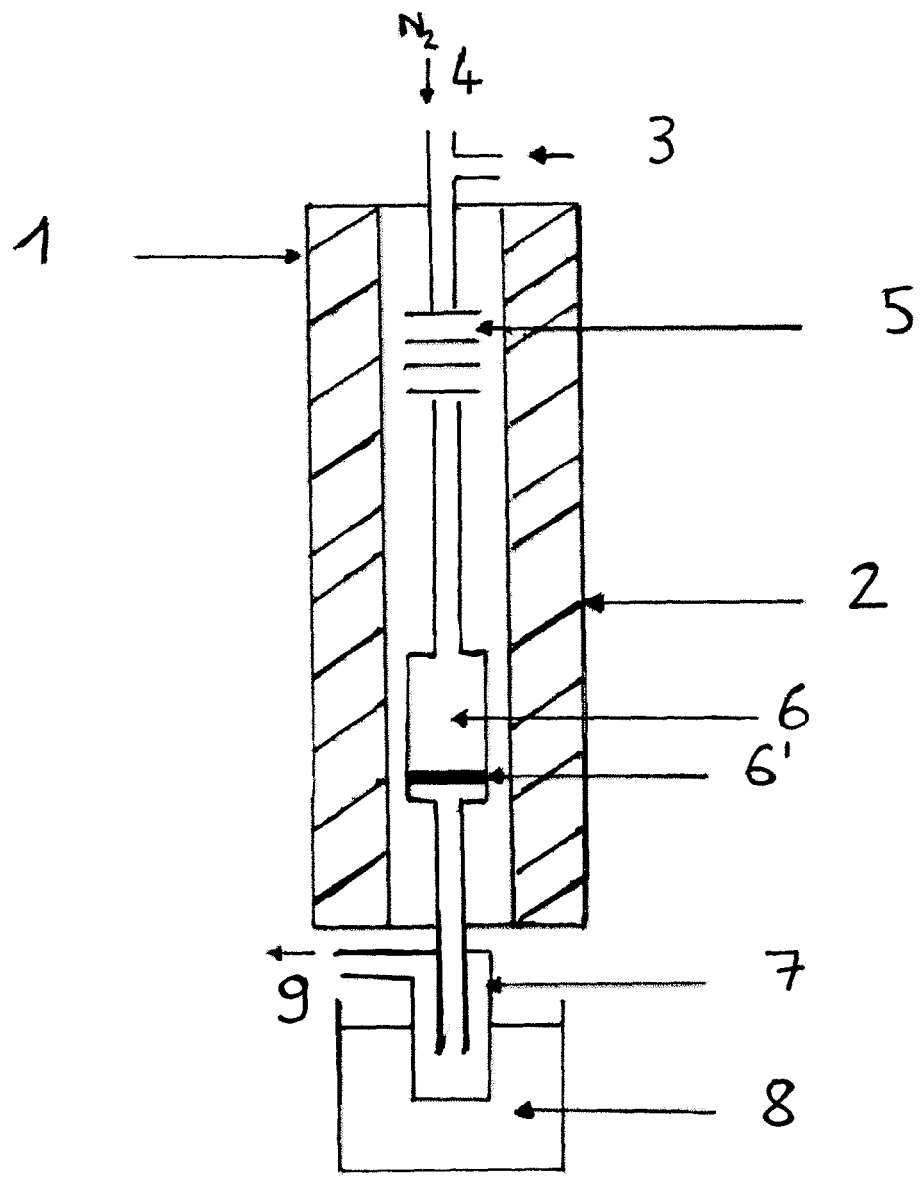

METHOD FOR PREPARING DIALKYLOXYDIANHYROHEXITOL BY ETHERIFICATION OF DIANHYDROHEXITOL USING A LIGHT ALCOHOL, IN THE PRESENCE OF AN ACIDIC CATALYST

FIELD OF THE INVENTION

The field of the invention is the O-alkylation of dianhydrohexitols.

In particular, the present invention relates to the preparation of ether derivatives of 1,4:3,6-dianhydrohexitol such as isosorbide, isoidide or isomannide.

More precisely, the invention targets a novel industrial process for etherification of these dianhydrohexitols by means of light alcohols such as methanol or ethanol, by acidic catalysis or bifunctional acid-metal catalysis, preferably in the gas phase.

TECHNOLOGICAL BACKGROUND AND PRIOR ART

The known 1,4:3,6-dianhydrohexitols are in particular: isosorbide, isomannide and isoidide of formula:

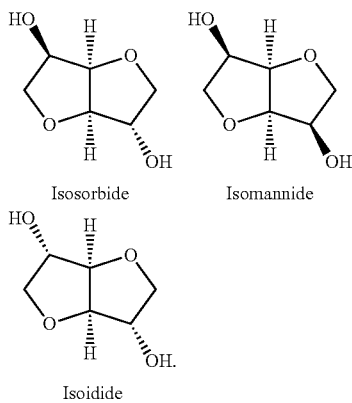

Also known are derivatives of isosorbide, isomannide and isoidide wherein the reactive —OH functions are replaced by reactive amine, acid or ether functions.

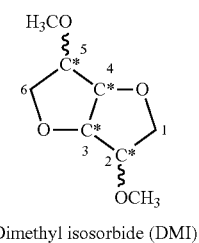

Dimethyl isosorbide (DMI)

is an example of an ether derivative of isosorbide. DMI is a recommended solvent in pharmaceutical and cosmetic compositions such as self-tanning, oral hygiene or anti-acne compositions, skin care creams, ointments and lotions. DMI is also a viscosity control agent. It can be used as a fluxing agent for bitumens.

The use of DMI in many fields other than the pharmaceutical and cosmetic industry is in particular described in the Applicant's international applications WO 2006/120342 and WO 2006/120343.

DMI is typically prepared by methylation of isosorbide with a methylating agent such as dimethyl sulfate or methyl chloride, in the presence of an alkaline agent such as soda. For economic reasons, methyl chloride is a particularly advantageous methylating agent. It is in fact available on the market in large quantities and at a cost lower than that of the brominated or iodinated equivalents. Thus the patent application EP 0 092 998 describes the methylation of isosorbide with methyl chloride (MeCl) in the presence of sodium or potassium hydroxide. The reaction described is performed in a water/aprotic organic solvent (DMSO or toluene) dispersion, bubbling in the gaseous methylating agent.

Although it affords high yields of DMI (90-95%), this methylation in an aqueous medium nonetheless poses the following problems:

(i) hydrolysis of the methylating agent. In fact, this undesirable side reaction reduces the ratio [MeCl bound/MeCl introduced], hereinafter referred to as the MeCl binding ratio, and leads to the formation of considerable quantities of salts, generally sodium chloride or potassium chloride, which must be removed at the end of the process (ii) gaseous reagent difficult to use (iii) toxicity of the methyl chloride reagent (iv) toxicity of the solvent (DMSO or toluene).

The use of dialkyl carbonate (dimethyl or diethyl) to obtain DMI from isosorbide does not involve these disadvantages (i), (ii), (iii) and (iv). This methylating agent is used both as reagent and "green" solvent. It is used in the presence of a basic catalyst. The reaction takes place at high temperatures and pressures and utilizes only one methyl group of the dimethyl carbonate, which adversely affects the economics of the process (U.S. Pat. No. 4,770,871; WO 2009/120703). In particular, this latter international patent application WO 2009/120703 describes a process for etherification of the dianhydrohexitol sugars in the presence of an O-alkylating agent which is a dialkyl carbonate.

There is thus a need for a clean method for synthesis of DMI and more generally of di, without generation of salts in particular, with an inexpensive and efficient methylating agent (without loss of carbon).

It must be noted that the prior art does not meet this need.

OBJECTIVES

In this context, the present invention aims to meet at least one of the objectives stated below.

One of the essential objectives of the present invention is to provide a novel improved process for preparing a composition based on dialkyloxydianhydrohexitols by etherification of dianhydrohexitols with at least one alkylating agent.

Another essential objective of the invention is to provide a novel, improved, simple and economical process for preparing a composition based on dialkyloxydianhydro-hexitols by etherification of dianhydrohexitols with at least one alkylating agent.

Another essential objective of the invention is to provide a novel improved process for preparing a composition based on dialkyloxydianhydrohexitols by etherification of dianhydrohexitols with at least one alkylating agent, said process not generating any troublesome side product.

Another essential objective of the invention is to provide a novel improved process for preparing a composition based on dialkyloxydianhydrohexitols by etherification of dianhydrohexitols with at least one inexpensive alkylating agent.

Another essential objective of the invention is to provide a novel improved process for preparing a composition based on dialkyloxydianhydrohexitols by etherification of dianhydrohexitols with at least one non-toxic, non-hazardous and ecologically compatible alkylating agent.

Another essential objective of the invention is to provide a novel improved process for preparing a composition based on dialkyloxydianhydrohexitols by etherification of dianhydrohexitols with at least one alkylating agent, said process being easy to industrialize and hence for example capable of being operated continuously.

Another essential objective of the invention is to provide a novel improved process for preparing a composition based on dialkyloxydianhydrohexitols by etherification of dianhydrohexitols with at least one alkylating agent, said process having favorable thermodynamics and hence good reaction kinetics.

Another essential objective of the invention is to provide a novel improved process for preparing a composition based on dialkyloxydianhydrohexitols by etherification of dianhydrohexitols with at least one alkylating agent, with good yields and good selectivity for dialkyloxydianhydrohexitols.

Another essential objective of the invention is to provide a novel improved process for preparing a composition based on dimethyl isosorbide by etherification of isosorbide with methanol, said process meeting at least one of the aforesaid objectives.

BRIEF DESCRIPTION OF THE INVENTION

These objectives, among others, are attained by the present invention which first of all relates to a method for preparing a composition based on dialkyloxydianhydrohexitols by etherification of dianhydrohexitols with at least one alkylating agent, in the presence of a solid catalyst, preferably a catalyst exhibiting Lewis acid or Brønsted acid properties, the etherification agent being selected from the group comprising, and better still consisting of:

- alcohols, preferably linear or branched aliphatic alcohols and, more preferably still, C1-C20 alcohols, better still methanol, ethanol, isopropanol or tert-butanol, methanol being particularly preferred,
- olefinic precursors of these alcohols,
- and mixtures thereof.

This efficient novel method is perfectly suited to industrial utilization. It enables the synthesis of methyl isosorbide ethers by reaction of isosorbide with methanol (or ethanol) in the presence of a solid acidic catalyst.

The method according to the invention is "clean", it circumvents the use of a methylating agent such as dimethyl sulfate or methyl chloride which generates stoichiometric quantities of salts. It also avoids the use of dialkyl carbonate, a more expensive methylating agent only one of whose two methyl groups is involved in the obtention of the mixed ethers of isosorbide.

DEFINITIONS

In the present description, any singular designates equally a singular and a plural and vice versa, unless otherwise stated.

The following definitions are given as examples for the understanding of the present description.

"dialkyloxydianhydrohexitol" is understood to mean a derivative of 1,4:3,6-dianhydrohexitol of formula III:

wherein:
$R^{10}$ and $R^{20}$ is an $-OR^{30}$ radical, the radicals $R^{30}$ being identical or different and each corresponding to an alkyl, preferably a linear or branched aliphatic alkyl and, still more preferably, a C1-C20 alkyl, better still methyl, ethyl, isopropyl or tert-butyl, methyl being particularly preferred, which corresponds to dimethyl isosorbide (DMI) as the compound of formula (III).

"O-alkylation" is understood to mean grafting of an alkyl onto a product by an ether bond.

"between x and y" is understood to mean a range or ranges of values the limits whereof are closed: [x,y].

"solid catalyst" is understood to mean a solid chemical compound which constitutes a distinct phase of the reaction phase capable of exerting an accelerating effect and a directing effect on the progress of a thermodynamically possible conversion and remaining unchanged at the end of the reaction and not being capable of modifying the thermodynamic equilibrium ("Catalyse de contact" [Contact Catalysis]—J. P. Le Page—Editions Technip, 1978, pages 1-2).

"supported solid catalyst" is understood to mean a solid catalyst consisting of an inert support of large specific area on which a catalytically active chemical compound is dispersed ("Catalyse de contact"—J. P. Le Page—Editions Technip, 1978, page 133).

"conversion", in particular "isosorbide conversion" (also written as "Isosorbide conv.") is understood to mean:
Isosorbide conv. (%)=100*(initial number of mole(s) of isosorbide−final number of mole(s) of isosorbide)/initial number of mole(s) of isosorbide.

"selectivity" (also written as sel.) is understood to mean:
Product i Sel. (mole %)=(100*No. moles of product i)/(sum No. moles of products i), i designating the isosorbide derivatives: DMI or MMI A or MMI B.

In the present application, the selectivity are thus calculated by normalization to 100 molar % for the isosorbide derivatives.

DETAILED DESCRIPTION OF THE INVENTION

Preferences

Preferred Embodiment

Gas Phase

In this preferred embodiment, the etherification is at least partly effected in the gas phase.

Performing the reaction in the gas phase enables in particular the obtention of colorless reaction products.

Catalyst

The catalyst is preferably selected from the group comprising and, better still, consisting of:

1. salts of heteropolyacids or polyoxometallates of general formula:

$$H_kX_jM_mO_n \cdot yH_2O \quad (I)$$

wherein,
X represents a heteroatom selected from the group consisting of the following elements: P, Si, Ge, B and As,
M represents a peripheral metallic element selected from the group consisting of W, Mo and V,
j is the number of heteroatoms and represents 1 or 2,
k is the number of hydrogen atoms and is between 0.5 and 10,
m is the number of peripheral metal atoms W, Mo and V and is between 1 and 18,
n is the number of oxygen atoms and is between 2 and 62,
y is the number of molecules of water of hydration and is between 0 and 40, preferably between 6 and 30, and mixtures thereof;

2. salts of alkali metals $Cs^+$, $K^+$, $Rb^+$ and ammonium ($NH_4^+$) salts, the latter being preferred, and mixtures thereof, 3. acidic catalysts based on zirconium oxide modified with oxo anions of the sulfate or tungstate type referred to as ZrS or ZrW possibly containing transition metals such as Fe, Mn and mixtures thereof, 4. zeolites, preferably selected from the group comprising and, better still, consisting of: H-beta, H-ZSM-5, MCM-22, H-USY, and mixtures thereof, 5. acidic clays of the montmorillonite type, phosphates such as Nb or zirconium phosphate, functionalized carbons, in particular carbons functionalized with sulfonic groups, 6. and mixtures thereof.

Preferably, for the catalyst, the salts of the heteropoly-acids (polyoxometallates) of general formula (I) are selected from the group comprising and, better still, consisting of: $H_3PW_{12}O_{40} \cdot 21H_2O$, $H_4SiW_{12}O_{40} \cdot 24H_2O$, $H_6P_2W_{18}O_{62} \cdot 24H_2O$, $H_5BW_{12}O_{40} \cdot 30H_2O$, $H_5PW_{10}V_2O_{40} \cdot yH_2O$, $H_3PMo_{12}O_{40} \cdot 28H_2O$, $H_4SiMo_{12}O_{40} \cdot 13H_2O$, $H_3PMo_6V_6O_{40} \cdot yH_2O$ and $H_5PMo_{10}V_2O_{40} \cdot yH_2O$, and mixtures thereof.

Advantageously, the solid catalyst is a supported catalyst.

Bifunctional Catalyst

According to an advantageous possibility afforded by the invention, the catalyst is a bifunctional metal-acid catalyst, that is to say that:

(i) the catalyst comprises a noble metal (preferably selected from the group comprising and, better still, consisting of gold, platinum, palladium and ruthenium, possibly modified by the addition of rhenium, osmium and iridium, titanium, zirconium, tantalum, or mixtures or alloys thereof), (ii) and the etherification is at least partly effected under a stream of hydrogen.

The use of a bifunctional metal-acid catalyst and the addition of hydrogen to the reagents stream, in particular when these are gaseous, makes it possible to stabilize the catalytic activity. This thus combats the loss of activity of the catalyst due for example to poisoning of the acidic sites by strong adsorption of oligomers. The bifunctional metal-acid catalyst enables the in situ hydrogenation of the precursors of these oligomers.

According to one possibility, the solid catalyst is selected from those having a differential heat of adsorption of ammonia (in kJ/mole) greater than or equal to 100, preferably 120 or, better still, between 120 and 200.

"Differential heat of adsorption of ammonia Qdiff" is understood to mean, for example, the quantity of heat dQ released by the adsorption of an infinitely small quantity of gaseous ammonia do at constant temperature on the catalyst initially under vacuum Qdiff=dQ/dn expressed in kJ/mole according to "Les techniques physiques d'etude des catalyseurs" [Physical techniques for the study of catalysts]—Editions Technip—Editors B. Imelik and J. C. Vedrine, 1988, as hereinafter defined in the examples.

Catalyst Regeneration

Another advantageous means of combating the loss of activity of the catalyst is to include a solid catalyst regeneration stage, preferably by treatment under $O_2$ at high temperature, in the process.

"High regeneration temperature" for example refers to temperatures (° C.) of between, in increasing order of preference, 400 and 600° C. or better still 450 and 500° C.

Cycles of regeneration of the used catalyst by treatment under oxygen at high temperature make it possible to regenerate its activity and endow it with resistance to poisoning.

Reagents

According to a preferred embodiment of the invention,
the dianhydrohexitols comprise a derivative of 1,4:3,6-dianhydrohexitol of formula II:

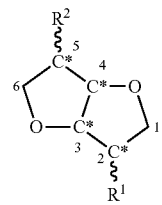

(II)

wherein:
$R^1$ and $R^2$ is an —$OR^3$ radical, the radicals $R^3$ being identical or different and each corresponding to H or an alkyl, and the dialkyloxydianhydrohexitols comprise a derivative of 1,4:3,6-dianhydrohexitol of formula III:

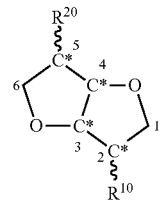

(III)

wherein:
$R^{10}$ and $R^{20}$ is an —$OR^{30}$ radical, the radicals $R^{30}$ being identical or different and each corresponding to an alkyl, preferably a linear or branched aliphatic alkyl and, still more preferably, a C1-C20 alkyl, better still methyl, ethyl, isopropyl or tert-butyl, methyl being particularly preferred, which corresponds to dimethyl isosorbide (DMI) as the compound of formula (III).

The etherification agent is selected from the group comprising or, better still, consisting of:
alcohols, preferably linear or branched aliphatic alcohols, more preferably still C1-C20 alcohols, better still methanol, ethanol, isopropanol or tert-butanol, methanol being particularly preferred, the olefinic precursors of these alcohols, and mixtures thereof.

Quantitative Data

According to another outstanding characteristic of the invention, the [alkylating agent/dianhydrohexitol] mole ratio is less than or equal to, in increasing order of preference: 30, 25, 20, 10, 5, 4, 3, 2 or better still between 2 and 20.

Methodology

The process is preferably implemented according to a continuous or semi-continuous mode. The reaction is advantageously performed in a continuous reactor and in the gas phase at high temperature. "High reaction temperature" for example refers to temperatures (° C.) superior or equal to between, in increasing order of preference, 160-300 and better still between 180-240. Operating in a continuous reactor has the advantage of giving a colorless reaction product in contrast to operation in a batch reactor in the liquid phase, which is characterized by longer contact times, favorable to the formation of generally colored side products, probably oligomers of the dianhydrohexitols (e.g. isosorbide).

As regards the heating, it is advantageous that:

1. in a first stage, the dianhydrohexitol(s) is/are vaporized at a temperature of T1 (in ° C.) greater than or equal to 170, preferably 180, T1 still more preferably being between 190 and 300, 2. and in a second stage the etherification is effected with the alkylating agent at a temperature T2 (in ° C.) greater than or equal to T1, preferably greater than or equal to 180, T2 still more preferably being between 200 and 300.

According to an outstanding characteristic of the invention, the starting dianhydrohexitol(s) is/are melted in solution and/or derive(s) directly from the synthesis of dianhydrohexitol(s) from hexitol(s). The starting dianhydrohexitol(s) advantageously derive(s) directly from a purification stage performed during the synthesis of dianhydrohexitol(s) from hexitol(s), in particular a distillation stage. The dehydration of the hexitol can be catalyzed by the etherification catalyst in a single stage combining the dehydration of the hexitol to dianhydrohexitol and the etherification of the dianhydrohexitol.

Moreover, given that the reaction of etherification of dianhydrohexitols (e.g. isosorbide) is a consecutive reaction leading to the obtention of monoalkyl ethers (e.g. monomethyl ethers or monoethyl ethers) A and B and dialkyl ethers (e.g. dimethyl ether or diethyl ethers of isosorbide), it seemed advantageous, according to a particular embodiment of the invention, to install a loop for recycling reaction products in order to favor the obtention of the final products, namely the dialkyloxydianhydrohexitols (e.g. dimethyl isosorbide).

Applications

The method according to the invention is an industrial process utilizable by producers of hexitols such as sorbitol or of anhydrohexitol such as isosorbide. This process results in a composition based on dialkyloxydianhydrohexitols (e.g. ethers of isosorbide such as the dimethyl ether or the diethyl ether). These products have uses in particular as fluxing agents for bitumen, as solvent, or in pharmaceutical or cosmetic compositions.

Other details of the invention will appear more clearly in the light of the examples given below for illustration.

EXAMPLES

1. Apparatus 1.1 Liquid Phase

The reactor used is an autoclave equipped with a magnetic stirrer. The liquid reagents are introduced, the alcohol then the isosorbide, and finally the solid catalyst. The autoclave is inerted under 20 bar of argon. It is raised to the reaction temperature by means of electrical resistance heaters.

1.2 Gas Phase—Continuous Mode

This apparatus, shown on the appended FIG. 1, comprises:

1. a vaporization oven 2. a reaction oven in the extension of the vaporization oven 1

3. an inlet (duct and pump) for mixing the reagents 4. a nitrogen feed to inert the jackets of the vaporization oven 1 and reaction oven 2

5. a coil in the vaporization oven 1

6. a reaction chamber positioned in the reaction oven 2 and containing the catalyst 6

7. a condenser downstream of the reaction oven 2

8. a cooling bath associated with the condenser 7

9. and an outlet duct for the O-methylated isosorbide.

2. Reagents

The isosorbide (ROQUETTE FRERES) is stored in the refrigerator under an inert atmosphere. The methanol and ethanol are obtained from the supplier Aldrich.

3. Characterization Techniques Used

The analysis of the reaction products is performed by gas phase chromatography equipped with a DB1 30 m×0.32 mm column, after silylation by means of BSTFA (N,O-bis-(trimethylsilyltrifluoroacetamide)).

Example 1

O-Methylation of Isosorbide by Methanol in the Presence of an Acidic Potassium Salt of 12-Tungsto-Phosphoric Acid: $K_2HPW_{12}O_{40}$ in Batch Reactor, Liquid Phase The following quantities are introduced into the autoclave: catalyst=2 g, isosorbide=36 g, MeOH/isosorbide mole ratio=5. The catalyst is the acidic cesium salt of 12-tungstophosphoric acid: $K_2HPW_{12}O_{40}$.

At the start of the reaction, the atmosphere in the autoclave consists of 20 bar of Ar.

The reaction mixture is raised to two different temperatures: 180° C. or 200° C. The reaction time is 6 hrs.

At the end of the reaction, the reaction medium is cooled by means of an ice bath.

The liquid reaction products are separated from the reaction medium and analyzed by gas chromatography. The isosorbide conversion and selectivity are calculated in mole % (standardization to 100 mole % of the conversions and selectivity for the isosorbide derivatives).

The results are shown in table 1.

TABLE 1

Conversion and selectivity of the
etherification reaction of isosorbide with methanol
catalyzed by $K_2HPW_{12}O_{40}$ in batch reactor, in liquid
phase. Effect of the reaction temperature.

| T (° C.) | Isosorbide conversion (%) | Selectivity (mole %) | | |
|---|---|---|---|---|
| | | DMI | MMI B | MMI A |
| 180 | 26 | 7 | 46 | 35 |
| 200 | 34 | 9 | 35 | 37 |

Formation of the monomethylated compounds A and B (MMI A and MMI B) and of dimethyl isosorbide (DMI) is observed at 180° C. and 200° C. with the catalyst $K_2HPW_{12}O_{40}$. However, the selectivity for DMI is low, in particular lower than 10%.

In the liquid phase, the reaction mixtures obtained at both temperatures 180 and 200° C. are strongly colored.

The coloration intensifies with the increase in the reaction temperature.

Example 2

O-Methylation of Isosorbide by Methanol Catalyzed by an Acid Potassium Salt of 12-Tungstophosphoric acid: $K_2HPW_{12}O_{40}$ in Continuous Reactor, in Gas Phase The reaction is performed in the apparatus of FIG. 1.
The following experimental protocol was adopted:
sampling of the condensate at the end of one hour (1 hr) and four hours (4 hrs) of reaction,
cessation of pumping of the reaction mixture at the end of four hours of reaction.
The experimental conditions were as follows:
Catalyst: $K_2HPW_{12}O_{40}$, $m_{cata}$=2 g
$D_{liq}$=0.06 ml·min$^{-1}$
$D_{N2}$=8 ml·min$^{-1}$
$P_{methanol}$=600 torr
$P_{isosorbide}$=28 torr
$T_{vaporization}$=225° C.
$T_{reaction}$=225° C.
Methanol/isosorbide mole ratio=20
$ppH_{iso}$ (hr$^{-1}$)=isosorbide mass flow (g·hr$^{-1}$)/mass of catalyst (g)=0.26 hr$^{-1}$.
The results obtained are shown in table 2.

TABLE 2

O-methylation of isosorbide with methanol catalyzed by
$K_2HPW_{12}O_{40}$ in continuous reactor, in gas phase.

| | $K_2HPW_{12}O_{40}$ | |
|---|---|---|
| Sampling (hrs of reaction) | 1 hr | 4 hrs |
| Isosorbide conv. (%) | 57 | 32 |
| DMI Sel. (mole %) | 62 | 60 |
| MMI B Sel. (mole %) | 30 | 22 |
| MMI A Sel. (mole %) | 8 | 18 |

MMI = monomethyl isosorbide

After one hour of reaction, the isosorbide conversion (isosorbide conv.) is 57% with predominant formation of DMI. The selectivity for DMI (DMI Sel.) is 62%. Between hr and 4 hrs, the activity stabilizes at an isosorbide conversion level of about 32%.

Very good conversion of isosorbide to DMI is thus obtained in the gas phase compared to that obtained in the liquid phase (example 1). Moreover, no coloration of the reaction medium occurred in the gas phase reaction. This in particular indicates the absence of degradation of the reaction products in spite of a high reaction temperature.

Example 3

O-Methylation of Isosorbide by Methanol Catalyzed by Solid Acidic Zeolite Catalysts in Continuous Reactor, in Gas Phase, at High Temperature The reaction is performed in the same apparatus as that of example 2.
The following experimental protocol was adopted:
sampling of the condensate at the end of one hour and four hours of reaction,
cessation of pumping of the reaction mixture at the end of four hours of reaction, with maintenance of the nitrogen flow for 30 minutes.
The experimental conditions were as follows:
$m_{cata}$=2 g
$D_{liq}$=0.06 ml·min$^{-1}$
$D_{N2}$=8 ml·min$^{-1}$
$P_{methanol}$=600 torr
$P_{isosorbide}$=28 torr
$T_{vaporization}$=225° C.
$T_{reaction}$=205° C.
Methanol/isosorbide mole ratio=20
$ppH_{iso}$ (hr$^{-1}$)=isosorbide mass flow (g·hr$^{-1}$)/mass of catalyst (g)=0.26 hr$^{-1}$.
The results obtained after 1 hr and 4 hrs of reaction are shown in tables 3 and 4 respectively.

TABLE 3

O-methylation of isosorbide with methanol
catalyzed by solid acidic zeolite catalysts in
continuous reactor in gas phase. Results after 1 hr of reaction.

| Catalysts | Isosorbide conversion (%) | Selectivity (mole %) | | |
|---|---|---|---|---|
| | | DMI | MMI B | MMI A |
| Beta | 78 | 34 | 54 | 12 |
| ZSM5 | 76 | 33 | 54 | 13 |
| MCM-22 | 51 | 9 | 73 | 18 |
| USY | 70 | 35 | 47 | 18 |

The zeolites catalyze the etherification of isosorbide by MeOH. The proportion of dimethyl ether formed by intramolecular dehydration depends on the zeolite.

TABLE 4

O-methylation of isosorbide with methanol
catalyzed by soild acidic zeolite catalysts in
continuous reactor in gas phase. Results after 4 hrs of reaction.

| Catalysts | Isosorbide conversion (%) | Selectivity (mole %) | | |
|---|---|---|---|---|
| | | DMI | MMI B | MMI A |
| Beta | 42 | 16 | 51 | 33 |
| ZSM5 | 31 | 14 | 47 | 39 |
| MCM-22 | 8 | 2 | 50 | 48 |
| USY | 35 | 28 | 43 | 37 |

After 4 hrs of reaction, the acidic zeolite catalysts exhibit lower activity which is accompanied by a decrease in the selectivity for dimethyl isosorbide. However, the Applicant has sought to remedy these disadvantages by increasing the residence time in the catalytic bed (example 5) and/or by using bifunctional metal-acid catalysts.

Example 4

O-Methylation of Isosorbide by Methanol Catalyzed by Solid Acidic Non-Zeolite Catalysts in Continuous Reactor in Gas Phase at High Temperature The following catalysts are evaluated:

tungstized zirconia: ZrW sulfated zirconia: ZrS sulfeted zirconia doped with Fe and Mn: ZMFS The reaction is performed in the apparatus described in example 2.

The following experimental protocol was adopted:

sampling of the condensate at the end of 1 hr and 4 hrs of reaction, cessation of pumping of the reaction mixture at the end of four hours of reaction, with maintenance of the nitrogen flow for 30 minutes.

The experimental conditions are the same as those of example 3.

The results obtained after 1 hr and 4 hrs of reaction are shown in tables 5 and 6 respectively.

TABLE 5

O-methylation of isosorbide with methanol catalyzed by solid acidic catalysts ZrS, ZrW and ZMFS in continuous reactor in gas phase. Results after 1 hr of reaction.

| Catalysts | Isosorbide conversion (%) | Selectivity (mole %) | | |
|---|---|---|---|---|
| | | DMI | MMI B | MMI A |
| ZrS | 42 | 38 | 43 | 19 |
| ZMFS | 68 | 20 | 55 | 25 |
| ZrW | 63 | 37 | 42 | 21 |

The Zr-based acidic catalysts catalyze the etherification of isosorbide by MeOH to methyl ethers.

TABLE 6

O-methylation of isosorbide with methanol catalyzed by solid acidic catalysts ZrS, ZrW and ZMFS in continuous reactor in gas phase. Results after 4 hrs of reaction.

| Catalysts | Isosorbide conversion (%) | Selectivity (mole %) | | |
|---|---|---|---|---|
| | | DMI | MMI B | MMI A |
| ZrS | 25 | 13 | 52 | 35 |
| ZMFS | 9 | 0 | 47 | 53 |
| ZrW | 38 | 11 | 52 | 37 |

As in the case of the zeolite catalysts, the zirconia-based acidic catalysts appear to exhibit deactivation during their functioning, and this is also accompanied by a decrease in the selectivity for dimethyl isosorbide.

Example 5

O-Methylation of Isosorbide by Methanol Catalyzed by H-ZSM5 Zeolite in Continuous Reactor in Gas Phase at High Temperature. Recycling of the Products The products of isosorbide etherification with methanol obtained at the end of a reaction of 4 hrs conducted under the conditions of example 3 are introduced into the reactor for a new reaction cycle under identical conditions. The reaction conditions are the same as those described in example 3.

The results obtained are shown in table 7.

TABLE 7

Composition of the reaction medium after a first pass then a second pass (recycling of the products) over the catalytic bed.

| | Mole % | | | |
|---|---|---|---|---|
| | MMI B | MMI A | DMI | Isosorbide |
| 1$^{st}$ pass | 25 | 13 | 6 | 56 |
| 2$^{nd}$ pass | 32 | 14 | 19 | 35 |

The recycling of the reaction products over the catalytic bed makes it possible to increase the conversion of the isosorbide and, in particular, the formation of DMI.

The conversion is thus only limited by the residence time in the reactor. A first improvement to be considered would consist in multiplying the catalytic bed in order to increase the residence time of the reagents in the catalytic bed and thus to increase the conversion level. Industrially, it would be a matter of using columns with a greater content of catalyst in order to achieve higher, in particular near quantitative, conversion levels.

Example 6

O-Methylation of Isosorbide by Methanol Catalyzed by H-ZSM5, ZrS and ZrW, Variation in Catalytic Activity with Time The experimental conditions are as follows:

$m_{cata}=2$ g $P_{isosorbide}=14$ torr $T_{vaporization}=185°$ C.

$T_{reaction}=200°$ C.

Methanol/isosorbide mole ratio=20

$ppH_{iso}$ (hr$^{-1}$)=0.39 g iso.g cata$^{-1}$.hr$^{-1}$.

The reaction time is 8 hrs with sampling every 2 hrs.

TABLE 8

Variation in isosorbide conversion with time.

| | Isosorbide conversion % | | | |
|---|---|---|---|---|
| Catalysts | 2 hrs | 4 hrs | 6 hrs | 8 hrs |
| ZrS | 61 | 30 | 13 | 5 |
| ZSM5 | 53 | 30 | 21 | 17 |
| ZrW | 25 | 13 | 1 | 0 |

Whatever the catalyst, the activity decreases with the reaction time. However, ZSM5 exhibits significantly higher activity than ZrS and ZrW. Moreover, the activity of ZSM5 stabilizes around 20% isosorbide conversion after 6 hrs of reaction.

Example 7

O-Methylation of Isosorbide by Methanol Catalyzed by a Bifunctional Metal-Acid Catalyst: Pt Dispersed on H-ZSM5 in the Presence of Hydrogen The bifunctional catalyst is prepared by nascent humidity impregnation of 1% Pt by weight onto the H-ZSM-5.
The reaction conditions are the same as those of example 6.
The results are shown in table 9.

TABLE 9

O-methylation of isosorbite by methanol catalyzed by Pt/H-ZSM-5 in the presence of hydrogen.

| Mole % | Isosorbide conversion % | | | |
|---|---|---|---|---|
| | 2 hrs | 4 hrs | 6 hrs | 8 hrs |
| Conversion | 83 | 72 | 61 | 55 |
| DMI Sel. | 32 | 27 | 21 | 18 |
| MMI B Sel. | 59 | 54 | 50 | 49 |
| MMI A Sel. | 9 | 19 | 29 | 33 |

Compared to the monofunctional acidic catalyst H-ZSM-5 (example 6), the addition of Pt to the H-ZSM-5 catalyst coupled with the presence of $H_2$ in the stream makes it possible to limit the rate of deactivation of the catalyst with time while limiting the decrease in the selectivity for DMI. Moreover, it is probable that optimization of the acidic function/metallic function balance of the catalyst, as well as optimization of the $pph_{iso}$, could make it possible to limit the deactivation and stabilize the activity.

Example 8

O-Ethylation of Isosorbide by Ethanol in Gas Phase Catalyzed by H-ZSM-5

The reaction conditions are the same as those of example 3. The ethanol/isosorbide mole ratio is 20. The results are shown in table 10.

TABLE 10

O-ethylation of isosorbide by ethanol catalyzed by Pt/H-ZSM-5 in the presence of hydrogen.

| Time | Isosorbide conversion (%) | Selectivity (mole %) | | |
|---|---|---|---|---|
| | | DEI | MEI B | MEI A |
| 0 hrs-1 hr | 47 | 23 | 55 | 22 |
| 1 hr-4 hrs | 40 | 15 | 57 | 28 |

The O-ethylation of isosorbide by ethanol can be performed in a continuous reactor in the gas phase at high temperature in the presence of the catalyst H-ZSM5. The results obtained at the end of one hour demonstrate the formation of diethyl isosorbide (DEI) and of monoethylated compounds. A decrease in the activity and the selectivity for DEI appears with time. However, the deactivation is less pronounced than in the presence of MeOH.

The invention claimed is:

1. A method for preparing a composition based on dialkyloxydianhydrohexitols by etherification of dianhydrohexitols with at least one O-alkylating agent, in the presence of a solid catalyst exhibiting Lewis acid or Bronsted acid properties and wherein the etherification agent is selected from the group consisting of:
   alcohols,
   olefinic precursors of said alcohols,
   and mixtures thereof.

2. The method as claimed in claim 1, wherein the etherification is at least partly effected in gas phase.

3. The method as claimed in claim 1, wherein the catalyst is selected from the group consisting of:
   salts of heteropolyacids and polyoxometallates of formula:

$$H_kX_jM_mO_n \cdot yH_2O \quad (I)$$

wherein,

X represents a heteroatom selected from the group consisting of the following elements: P, Si, Ge, B and As, M represents a peripheral metallic element selected from the group consisting of W, Mo and V, j is the number of heteroatoms and represents 1 or 2, k is the number of hydrogen atoms and is between 0.5 and 10, m is the number of peripheral metal atoms W, Mo and V and is between 1 and 18, n is the number of oxygen atoms and is between 2 and 62, y is the number of molecules of water of hydration and is between 0 and 40, and mixtures thereof, salts of alkali metals $Cs^+$, $K^+$, $Rb^+$ and ammonium $NH_4^+$ salts and mixtures thereof, acidic catalysts based on zirconium oxide modified with oxo anions of the sulfate or tungstate zeolites, acidic clays of the montmorillonite type, phosphates functionalized carbons, and mixtures thereof, and mixtures thereof.

4. The method as claimed in claim 3, wherein for the catalyst the salts of the heteropolyacids of formula (I) are selected from the group consisting of:

$H_3PW_{12}O_{40} \cdot 21H_2O$, $H_4SiW_{12}O_{40} \cdot 24H_2O$, $H_6P_2W_{18}O_{62} \cdot 24H_2O$, $H_5BW_{12}O_{40} \cdot 30H_2O$, $H_5PW_{10}V_2O_{40} \cdot yH_2O$, $H_3PMo_{22}O_{40} \cdot 28H_2O$, $H_4SiMo_{12}O_{40} \cdot 13H_2O$, $H_3PMo_6V_6O_{40} \cdot yH_2O$, $H_5PMo_{10}V_2O_{40} \cdot yH_2O$, and mixtures thereof.

5. The method as claimed in claim 1, wherein the catalyst is supported.

6. The method as claimed in claim 1, wherein the catalyst comprises a noble metal,
   and the etherification is at least partly effected under a stream of hydrogen.

7. The method as claimed in claim 1, further comprising a solid catalyst regeneration stage.

8. The method as claimed in claim 1, wherein the dianhydrohexitols comprise a derivative of 1,4:3,6-dianhydrohexitol of formula II:

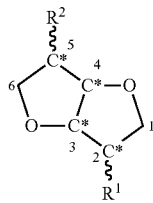
(II)

wherein:
$R^1$ and $R^2$ is an —$OR^2$ radical, the radicals $R^3$ being identical or different and each corresponding to H or an alkyl,
and the dialkyloxydianhydrohexitols comprise a derivative of 1,4:3,6-dianhydrohexitol of formula III:

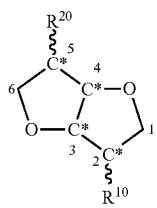
(III)

wherein:
$R^{10}$ and $R^{20}$ is an —$OR^{20}$ radical, the radicals $R^{20}$ being identical or different and each corresponding to an alkyl.

9. The method as claimed in claim 1, wherein the [alkylating agent/dianhydrohexitol] mole ratio is less than or equal to 30.

10. The method as claimed in claim 1, wherein:
1. in a first stage, the dianhydrohexitol(s) is/are vaporized at a temperature of T1 (in ° C.) greater than or equal to 170 and
2. in a second stage, the etherification is effected with the alkylating agent at a temperature T2 (in ° C.) greater than or equal to T1.

11. The method as claimed in claim 1, wherein the starting dianhydrohexitol(s) is/are melted in solution and/or derive(s) directly from the synthesis of dianhydrohexitol(s) from hexitol(s).

12. The method as claimed in claim 1, wherein as the starting product(s), one (of the) hexitol(s) is/are used, and in that the dehydration of the hexitol is catalyzed by the catalyst in a single stage combining the dehydration of the hexitol(s) to dianhydrohexitol(s) and the etherification of the dianhydrohexitol(s).

13. The method as claimed in claim 1, wherein the method is implemented according to a continuous or semi-continuous mode.

14. The method as claimed in claim 2, wherein the catalyst is selected from the group consisting of:
salts of heteropolyacids and polyoxometallates of formula:

$$H_kX_jM_mO_n \cdot yH_2O \quad (I)$$

wherein,
X represents a heteroatom selected from the group consisting of the following elements: P, Si, Ge, B and As,
M represents a peripheral metallic element selected from the group consisting of W, Mo and V,
j is the number of heteroatoms and represents 1 or 2,
k is the number of hydrogen atoms and is between 0.5 and 10,
m is the number of peripheral metal atoms W, Mo and V and is between 1 and 18,
n is the number of oxygen atoms and is between 2 and 62,
y is the number of molecules of water of hydration and is between 0 and 40,
and mixtures thereof,
salts of alkali metals $Cs^+$, $K^+$, $Rb^+$ and ammonium $NH_4^+$ salts and mixtures thereof,
acidic catalysts based on zirconium oxide modified with oxo anions of the sulfate or tungstate,
zeolites,
acidic clays of the montmorillonite type, phosphates, functionalized carbons, and mixtures thereof,
and mixtures thereof.

\* \* \* \* \*